United States Patent [19]

Meier et al.

[11] 4,379,463

[45] Apr. 12, 1983

[54] MULTICENTRIC KNEE CAGE

[75] Inventors: Robert H. Meier; Evelyn Farr, both of Jackson, Mich.

[73] Assignee: Camp International, Inc., Jackson, Mich.

[21] Appl. No.: 253,047

[22] Filed: Apr. 13, 1981

[51] Int. Cl.³ .............................................. A61F 5/00
[52] U.S. Cl. .......................... 128/80 C; 128/DIG. 15; 128/88
[58] Field of Search ................. 128/80 C, 80 R, 80 F, 128/88, 87 R, DIG. 15, 165

[56] References Cited

U.S. PATENT DOCUMENTS

| 2,251,629 | 9/1939 | Manzeck | 2/24 |
|---|---|---|---|
| 2,460,895 | 2/1949 | Meany | 2/24 |
| 2,467,907 | 4/1949 | Peckham | 128/88 |
| 2,883,982 | 9/1956 | Rainey | 128/80 |
| 2,959,168 | 5/1957 | Shook | 128/80 |
| 3,387,305 | 2/1966 | Shafer | 2/22 |
| 3,653,378 | 4/1972 | Reuther | 128/88 |
| 3,786,804 | 1/1974 | Lewis | 128/80 C |
| 3,817,244 | 6/1974 | Taylor | 128/80 C |
| 3,935,858 | 2/1976 | Harroff | 128/80 |
| 4,013,070 | 3/1977 | Harroff | 128/80 |
| 4,090,508 | 5/1978 | Gaylord, Jr. | 128/80 |

OTHER PUBLICATIONS

The Canadian Physiological Knee Stabilizing Orthosis, Copyright 1979.

Primary Examiner—John D. Yasko
Attorney, Agent, or Firm—Beaman & Beaman

[57] ABSTRACT

The invention pertains to a knee cage for providing additional orthopedic support to the knee wherein a multicentric hinge is employed to permit natural knee flexure and high lateral support. A flexible cover of fabric having loops defined in the outer surface thereof is wrapped about the knee and held in an embracing manner by elastic straps. Hinge means each formed by a pair of hinge elements interconnected by multicentric pivot means are removably mounted upon lateral portions of the cover permitting the hinge means to be adjustably secured to the cover permitting optimum location thereon. Elongated elements of the hinge means are received within pockets having hooks defined thereon for cooperating with the cover loops to adjustably affix the hinge means to the cover.

13 Claims, 10 Drawing Figures

MULTICENTRIC KNEE CAGE

BACKGROUND OF THE INVENTION

The human knee is subjected to a wide variety of compressive, bending, twisting and lateral forces, particularly when engaging in sports, and appliances such as knee braces or cages supporting the knee are widely used. Knee braces in their simplest form, comprise a sleeve of elastic fabric which receives the knee region, permits bending, but provides external mechanical support and bracing.

Knee cages often include stays or stiffening means, leg encircling straps are commonly used, and in order to provide lateral strength and support hinges are often incorporated into the cage.

Difficulty is encountered when using hinges with knee braces or cages in that the natural hinge interconnection between the femur and tibia does not produce pivoting about a fixed axis, but rather, a rolling interconnection occurs across the knee cartilage and a fixed pivot axis is not present. Accordingly, hinge devices used with knee braces and cages must accommodate the natural hinging action if the cage is not to interfere with normal knee use, and various types of hinges are employed with knee cages.

In prior art knee cages and braces using a flexible cover the hinge means are usually incorporated into the knee cover, such as by sewing, wherein the relationship of the hinge means to the cover is fixed. Such a fixed hinge does not permit accommodations of variations in knee structure and requires that the cage be accurately located upon the knee in order to achieve maximum comfort. The location of the cage cover on the knee to permit optimum hinge operation may not coincide with the desired locating of the cover with respect to the user's knee, and in such instances discomfort will result due to the necessity for the cover to be slightly displaced from the optimum position, or the hinge means will not be ideally located.

It is an object of the invention to provide a knee cage of the wrap around type which may be readily placed upon the knee, and wherein hinge means are associated with the cage cover, and are adjustably positionable thereon in order to assure the optimum locating of the hinge with respect to the cage cover.

Another object of the invention is to provide a knee cage of a wrap around type which may be quickly placed upon the wearer's knee and provides excellent lateral support by means of a multicentric metal hinge.

A further object of the invention is to provide a wrap around knee cage utilizing metal hinge means which may be readily removed from, and attached to, the outer cover of the cage at a variety of locations to permit custom positioning of the hinge relative to the knee being supported.

Yet a further object of the invention is to provide a multicentric hinge for knee braces and cages wherein multicentric pivoting between rigid hinge elements is achieved, yet the hinge elements are maintained in parallel planar relationship and supported against relative lateral displacement.

In the practice of the invention a cover of trapezoidal configuration includes a soft foam inner surface, and an outer surface of fabric having loop means defined thereon. At the central region of the cover an opening is formed which is located behind the knee to augment the cover flexibility during knee bending.

Four elastic straps are sewn to the cover at their inner ends, and the outer ends include hooks for cooperating with the cover outer surface loop means whereby the cover, and its straps, may be quickly wrapped about the knee.

The cage cover includes lateral portions disposed at the sides of the knee, and hinge means are located at such lateral portions. The hinge means each consist of a pair of elongated rigid metal elements interconnected by a multicentric pivot arrangement, and the hinge elements are each received within a pocket having hook means defined on the inner surface thereof, and loop means defined on the exterior surface. Thus, upon the hinge element pockets gripping the loop means of the cover lateral portions the cage hinges can be located upon the lateral portions as desired in such a manner to provide excellent lateral support of the knee and the adjustable locating, and multicentric pivoting, minimizes interference of knee movement by the hinge.

The multicentric hinge of the invention includes metal elements each having a flat inner end, and one of the elements includes a bearing plate located in spaced parallel relationship to the inner end wherein the other element inner end is disposed intermediate the bearing plate and associated inner end. Pins supporting the bearing plate are received within an irregularly shaped cavity in the other element inner end, and this cavity includes a recess portion which defines a fulcrum when receiving a pin therein. The dimensions and spacing of the pins in relationship to the cavity configuration is such that the pins and cavity permit multicentric pivoting between the hinge elements between desired angular limits, and the hinge will support the knee against excessive angular pivoting, as well as provide lateral support.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENT

Figure 1:
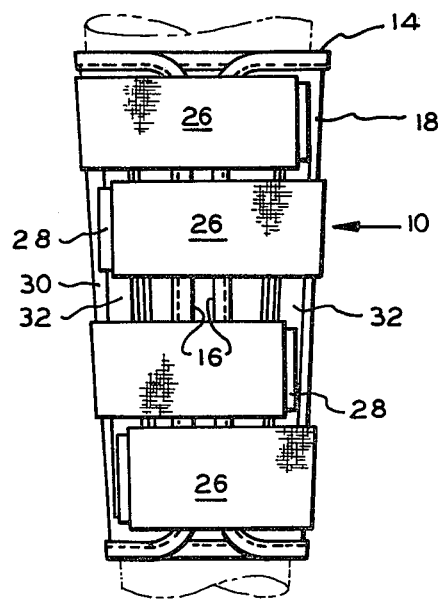
FIG. 1 is a front, elevational view of a knee cage in accord with the invention as wrapped about a knee.
Figure 2:
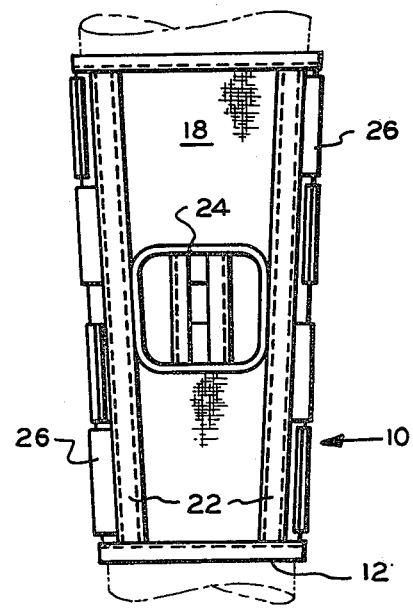
FIG. 2 is a rear elevational view of the knee cage.
Figure 3:
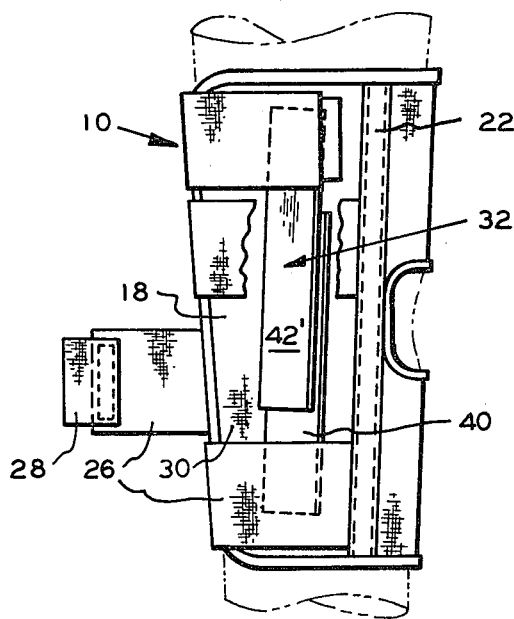
FIG. 3 is an elevational view of the left side, one of the straps being unfastened for purpose of illustration.
Figure 5:
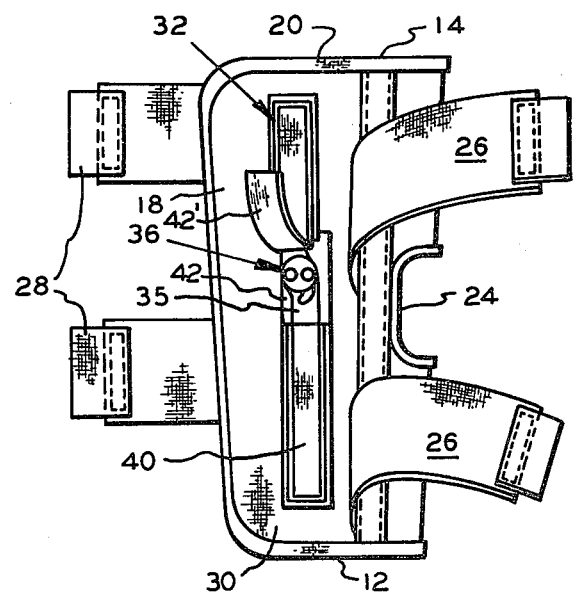
FIG. 5 is a elevational view of the left side of the cage, the straps being unfastened, and the hinge inner ends being exposed.
Figure 4:
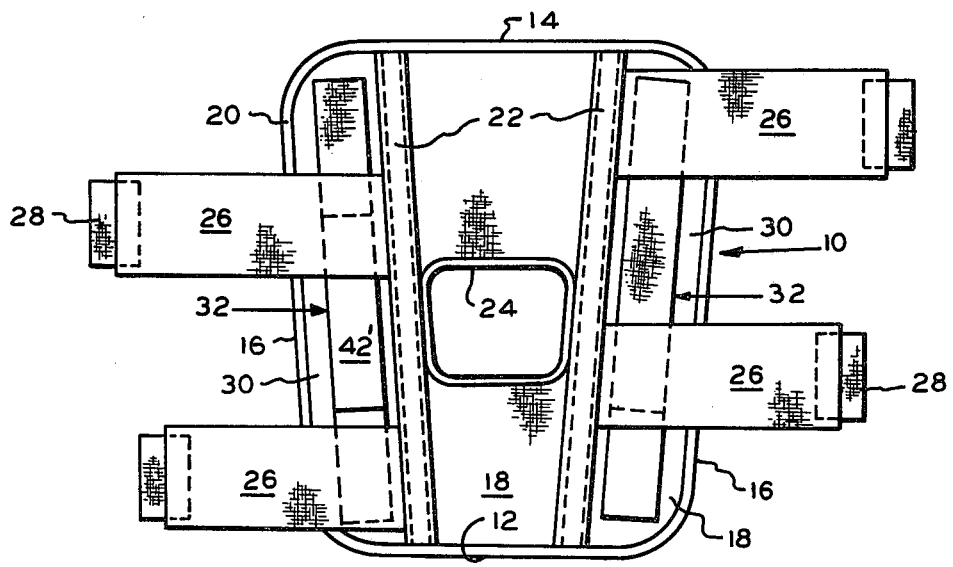
FIG. 4 is a plan outer view of the cage cover laid out in a planar manner, with the straps extended.

The general configuration of a knee cage in accord with the invention is best appreciated from FIG. 4 wherein the cage is laid out in a planar manner. The cover, generally indicated at 10, is of a trapezoidal configuration having a lower edge 12, an upper edge 14, and lateral edges 16. The upper and lower edges, and associated lateral edges, are interconnected by tangential radiused corners. The cover 10 is formed of a flexible fabric, and on its inner surface, it is preferably provided with a soft foam which directly engages the skin in a comfortable manner. The outer surface of the cover is formed with a fabric 18 having loop means defined thereon such as is commonly employed with fastening systems sold under the trademark "Velcro". The inner and outer surfaces of the cover are bound together at their periphery by binding 20, and fabric ribs 22 are sewn both to the inner and outer surfaces between edges 12 and 14. Centrally, the cover is provided with an opening 24 having a binding thereabout, the central opening being located behind the knee, when in use, to augment flexibility.

Four flexible straps 26 of elastic material are sewn to the exterior surface of the cover 10. The inner ends of the straps are each sewn to the reinforcing ribs 22, and the outer ends of the straps are each provided with a Velcro hook patch 28 having hooks formed thereon for permitting the outer end of the straps to be removably attached to the cover loop surface 18. As will be appreciated from FIGS. 1-5, the straps 26 are of different lengths, extend in alternate directions with respect to the cover 10, and are circumferentially misaligned whereby the straps do not interfere with each other when encircling the knee and cover.

Cover lateral portions 30 are defined intermediate the opening 24, and the lateral edges 16. These lateral portions receive the hinge assemblies generally indicated at 32, the hinge assemblies being located "beneath" the straps 26 extending over the lateral portions 30.

The hinge assembly 32 is of an elongated form and of a length less than the vertical dimension of the cover 10, as will be appreciated from the drawings.

Figure 6:
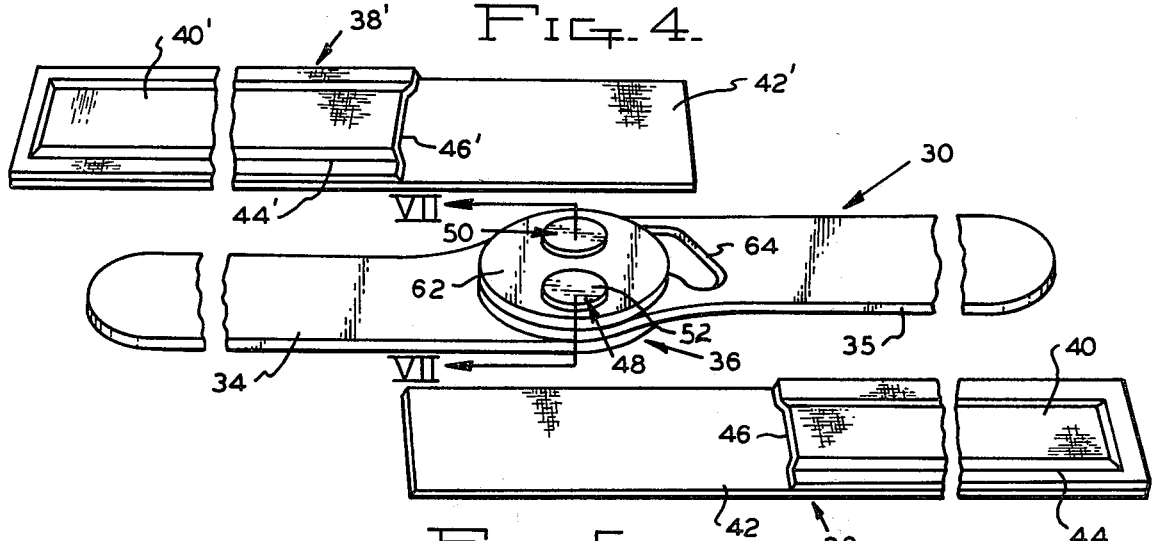
FIG. 6 is an exploded, perspective view of the hinge and its pockets.
Figure 7:
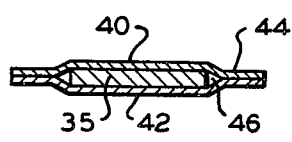
FIG. 7 is an elevational view taken through a hinge element having a pocket mounted thereon.
Figure 8:
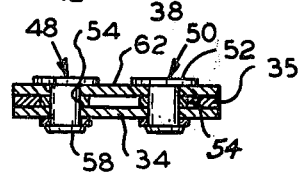
FIG. 8 is an elevational sectional view taken through the hinge element inner ends taken along Section VIII—VIII of FIG. 6.

The hinge assemblies each include a pair of substantially rigid metal elements 34 and 35 of elongated form interconnected by multicentric pivot means generally indicated at 36. Each element is received within a pocket 38 or 38', and each pocket including an inner portion 40 sewn to an outer portion 42, as at 44. The inner portion 40 is of a length substantially less than the outer portion 42, FIG. 6, and the length of the inner portion 40 is slightly less than the length of the elements 34 and 35 extending from the pivot means 36. In one pocket 38 the inner portion 40 is formed of a Velcro loop material, while the outer portion 42 is of a Velcro hook material, and a cavity 46 is defined between the inner and outer portions for closely receiving an element 34 or 35. In FIG. 6, pocket 38 receives element 35. In the other pocket 38' the inner portion 40' is formed of a Velcro hook material while the longer portion 42' has loops defined upon its outer surface and cavity 46' is defined therebetween. In FIG. 6 the pocket 38' is rotated over toward element 34 180° and element 34 is inserted into cavity 46'.

With the elements 34 and 35 received within the pockets 38' and 38, as described above, the hooks of portions 42 and 40' will be disposed on the "underside" of the hinge assembly 32, FIG. 6, while the loop material of portions 40 and 42' will be located on the "upperside" of the hinge assembly. The aforedescribed assembly of hinge assembly 32 is for the hinge assembly located on the left side of the cage as worn, as in FIGS. 3 and 5. When assembling the pockets and hinge elements for the right hinge assembly the pockets are rotated 180° with respect to the described assembly and mounted upon the same elements 35 and 34.

With the hinge elements 34 and 35 each closely received within their pocket 38 or 38' the portion 42 will extend over pivot 32 on the inside and portion 42' will extend over pivot 32 on the outside and the hinge assembly may be affixed to a lateral portion 30 by the hooks of portions 40 and 42' cooperating with the loop means of the cover material 18 of lateral portions 30. Thus, the hinge assemblies 32 may be adjusted toward or away from the lateral edges 16, and vertically with respect to the edges 12 and 14 to locate the hinge assemblies as desired upon the cover 10.

In use, the knee cage cover 10 is opened as in FIG. 4, and the inner surface thereof is placed against the back of the knee, with the opening 24 directly behind the knee cap. The straps 26 are then wrapped toward the front of the knee, and the straps will be slightly stretched, and the hook patches 28 are applied to the opposite cover lateral portions 30 and the outer surfaces of the pocket portions 42 and 40'. Of course, the covers 10 will be made in various sizes of individuals. In this manner the knee cage will firmly encompass the knee both above and below the joint, and by previously locating the hinge assemblies 32 upon the associated lateral portions 30, as desired, the most comfortable fit and most efficient orientation of the hinge means upon the cage may be achieved. The use of the elastic straps 26 and hook and loop fasteners permits the cage to be quickly wrapped around and attached to the knee and firm support is provided.

The hinge elements 34 and 35 may be formed of aluminum, and are preferably flat in configuration, the outer end being radiused, and the inner end being flat and each having a circular periphery. The inner end of the element 34 is provided with a pair of holes which receive a pair of rivet pin assemblies 48 and 50 which are headed at 52, include washer spacers 54 and are headed over at 58. The pins 48 and 50 extend through and hold flat circular bearing plate 62 in spaced parallel relationship to the inner end of element 34 by the pins.

The spacing between the inner end of element 34 and the bearing plate 62 is only slightly greater than the thickness of the inner end of element 35, and the inner end of element 35 is received therebetween in a sliding pivotal manner. The inner end of element 35 includes an irregularly shaped cavity 64 whose configuration will be appreciated from FIGS. 9 and 10, and the pins 48 and 50 extend through the cavity as will be appreciated from the drawings. The cavity recess 66 defines a fulcrum recess when the pin 48 is received therein as in FIG. 9, and the cavity surface 68 forms an abutment surface against which pin 50 engages when the elements 34 and 35 are related as in FIG. 9. When the elements 34 and 35 are pivoted to each other such as shown in FIG. 10 a relationship between the pins and cavity such as illustrated in FIG. 10 occurs, and it will be appreciated that the transverse dimensional relationship between the cavity 64 and the pins 48 and 50 is such that a multicentric pivoting between the elements 34 and 35 occurs within the limits defined by the pins and cavity configuration.

Figure 9:
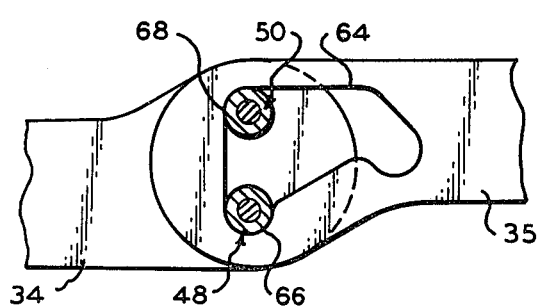
FIG. 9 is a plan view of the hinge inner ends, the bearing plate being removed for purpose of illustration, illustrating the hinge elements in a fulcrumed condition restricting maximum counterclockwise angular deviation.

The "straight" relationship between the elements 34 and 35 is illustrated in FIG. 9, and this relationship is that which occurs when the leg is substantially extended. The pin 48 is received within the cavity recess 66, and the pin 50 engages the abutment surface 68. Thus, with the hinge elements in the relationship of FIG. 9 further "counterclockwise" rotation of hinge element 34 with respect to element 35 is prevented, and the elements cannot be moved in any linear direction relative to each other, and the only movement permitted is a "clockwise" rotation of the element 34 relative to element 35 about fulcrum recess 66. With the hinge elements in the relationship shown in FIG. 9 the knee is supported against "reverse" hinging, and the knee protected against frontal forces, as well as lateral pressures.

The "locking" of the hinge against "reverse" hinging, of course, requires that the hinge assembly 32 on each side of the cage be oriented so that both hinge assemblies fully pivot in the proper direction. In this respect, no mechanical modification of the hinge apparatus is required for right and left hinged. It is only necessary to turn the pockets 38 and 38' 180° on the elements 35 and 34 so that the hooks of portions 42 and 40' be located on the inside of the hinge elements for cooperation with the loops on the outer surface 18 at the appropriate lateral portion 30.

Figure 10:
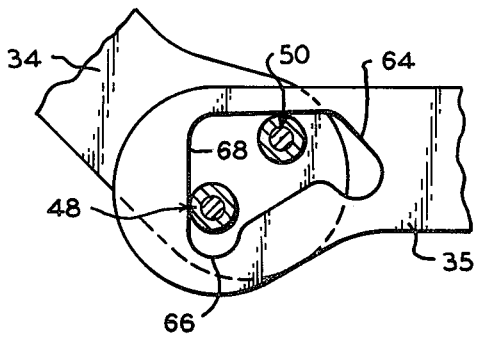
FIG. 10 is a view similar to FIG. 9, illustrating relative pivotal movement between the hinge elements.

Extensive pivoting between the elements 34 and 35 may occur when the elements are partially pivoted to each other as shown in FIG. 10, and this freedom of pivoting accommodates the "rolling" hinge action of the knee without binding resulting in a true multicentric action.

The fact that the inner end of element 35 is closely supported between the inner end of element 34 and the bearing plate 62 produces a strong connection between elements 34 and 35 in a direction at right angles to the planes of the elements to resist lateral deformation, which is particularly important with respect to contact sports.

As the hinge structure can be economically formed of stamped components the cost thereof is minimized, and merely by reversing the assembled hinge the same construction can be used upon opposite sides of the knee cage.

It is appreciated that various modifications to the inventive concepts may be apparent to those skilled in the art without departing from the spirit and scope of the invention.

We claim:

1. A knee cage for supporting the knee comprising, in combination, a flexible cover having upper, lower and lateral edges and inner and outer surfaces, said cover including lateral portions, cover securing means mounted upon said cover adapted to secure said cover about the wearer's knee, hinge means defined upon said cover lateral portions, said hinge means each including first and second elongated elements interconnected by a floating pivot, and hinge mounting means releasably mounting said hinge means elements upon said cover outer surface at said lateral portions to permit selective positioning of said hinge means upon the associated cover lateral portion.

2. In a knee cage as in claim 1, said hinge elements being formed of metal, pocket members having elongated pockets receiving each hinge element, said releasable hinge mounting means being defined upon said pocket members.

3. In a knee cage as in claim 2, loop means defined on said cover outer surface, said pocket members each including an inner surface, and hook means defined upon said pocket members' inner surface adapted to engage said cover loop means, said loop and hook means comprising said releasable hinge mounting means.

4. In a knee cage as in claim 1, said cover including a rear central portion, an opening defined in said cover rear central portion, said opening providing cover flexibility behind the wearer's knee.

5. In a knee cage as in claim 1, said hinge means floating pivot comprising a multicentric interconnection between interconnected elongated elements permitting relative pivoting of interconnected hinge elements about a floating pivot axis.

6. In a knee cage as in claim 5 wherein said hinge means pivot includes parallel bearing plate portions interconnecting said elongated elements, and stop means interposed between interconnected elements limiting the extent of pivoting therebetween.

7. In a knee cage as in claim 6, wherein said stop means comprises a pair of pins mounted on one of said elements and an irregular shaped cavity defined in the other interconnected element, said cavity including pin engageable abutments, said pins being located within said cavity.

8. A knee cage for supporting the knee comprising, in combination, a flexible cover having upper, lower and lateral edges and inner and outer surfaces, said cover including lateral portions, cover securing means mounted upon said cover adapted to secure said cover about the wearer's knee, loop means defined on said cover outer surface, hinge means defined upon said cover lateral portions upon said outer surface, said hinge means each comprising a pair of substantially rigid elongated elements having substantially flat inner ends, hook means defined upon said elements releasable affixing said elements to said outer surface loop means for selective positioning upon said cover lateral portions, and bearing plate means affixed to one of said element's inner ends pivotally interconnecting associated elements in a floating pivot multicentric manner.

9. In a knee cage as in claim 8, projection means defined upon the inner end of said one element, a cavity defined in the inner end of the other element, said projection means extending through said cavity, and abutment surfaces defined in said cavity engageable with said projection means limiting relative movement between interconnected elements.

10. In a knee cage as in claim 8, a pocket member receiving each of said hinge elements, said pocket members each having an inner surface engaging said cover outer surface, said hook means being defined upon said pocket members' inner surfaces.

11. A multicentric hinge for knee orthosis appliances comprising, in combination, first and second elongated substantially rigid elements each having a substantially flat inner end, a bearing plate affixed to said first element inner end is spaced parallel relationship thereto, said second element inner end being closely slidably supported between said first element inner end and said bearing plate whereby said second element is pivotally interconnected to said first element, a pair of spaced projections defined upon the inner end of said first element, a cavity defined upon the inner end of said second element, said projections extending within said cavity, and abutment surfaces defined within said cavity engageable by said projections limiting the extent of pivoting between said first and second elements.

12. In a multicentric hinge as in claim 11, said projections comprising a pair of pins defined upon said first element, said bearing plate being mounted upon said pins.

13. In a multicentric hinge as in claim 12, said cavity abutment surfaces including a pin receiving recess defining a fulcrum upon receiving a pin therein whereby a pin received within said recess pivots said first element with respect to said second element about half said recess until the other pin engages a cavity abutment surface.

* * * * *

UNITED STATES PATENT OFFICE
CERTIFICATE OF CORRECTION

Patent No. __4,379,463__  Dated __April 12, 1983__

Inventor(s) __Robert H. Meier, Evelyn Farr and James H. Tyo__

It is certified that error appears in the above-identified patent and that said Letters Patent are hereby corrected as shown below:

On the cover page:

In the identification of the inventors, add

-- James H. Tyo --

Column 8, line 4, delete "half"

Signed and Sealed this

*Thirty-first* Day of *May 1983*

[SEAL]

Attest:

DONALD J. QUIGG

*Attesting Officer*  *Acting Commissioner of Patents and Trademarks*